(12) United States Patent
Wang

(10) Patent No.: US 6,730,377 B2
(45) Date of Patent: May 4, 2004

(54) BALLOONS MADE FROM LIQUID CRYSTAL POLYMER BLENDS

(75) Inventor: Lixiao Wang, Long Lake, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 13 days.

(21) Appl. No.: 10/055,585

(22) Filed: Jan. 23, 2002

(65) Prior Publication Data

US 2003/0138577 A1 Jul. 24, 2003

(51) Int. Cl.$^7$ .......................... B32B 1/08; A61M 29/02; A61M 25/10; A61M 39/00; C08F 20/52
(52) U.S. Cl. .................. 428/35.7; 428/36.9; 428/36.91; 604/509; 604/96.01; 604/264; 604/915; 525/437; 525/444; 525/450; 525/540
(58) Field of Search ................................ 428/35.7, 36.9, 428/36.91; 604/509, 96.01, 264, 915; 525/437, 444, 450, 540

(56) References Cited

U.S. PATENT DOCUMENTS

| 3,991,014 A | 11/1976 | Kleinschuster | 260/47 |
|---|---|---|---|
| 4,067,852 A | 1/1978 | Calundann | 260/47 |
| 4,083,829 A | 4/1978 | Calundann et al. | 260/47 |

(List continued on next page.)

FOREIGN PATENT DOCUMENTS

| EP | 0 369 734 | 5/1990 |
|---|---|---|
| EP | 0 448 886 A1 | 2/1991 |
| EP | 0 934 755 A2 | 11/1999 |
| JP | 2-159247 A | 6/1990 |
| WO | 91/08281 | 6/1991 |
| WO | 92/19316 | 11/1992 |
| WO | 92/19440 | 11/1992 |
| WO | 93/24574 | 12/1993 |
| WO | 95/23619 | 9/1995 |
| WO | 96/00752 | 1/1996 |
| WO | 96/04951 | 2/1996 |
| WO | 97/24403 | 7/1997 |
| WO | 00/50105 | 8/2000 |

OTHER PUBLICATIONS

Xydar ®product data, Sep., 1994.
J.M. Schultz, "Structure Evolution in PET Fiber", *Polymer Preprints*, 304–306 Apr. 1992.
Y. Yang et al., Orientation and Strain–Induced Liquid–Crystalline Phase Transition of Networks of Semi–Rigid Chains, *Polymer Preprints*, 729–730, Aug. 1993.
R. Stadler and T. Oehmichen, "Telechelic Oligoaramides—A Means For Rigid–Rod Molecular Inforcement of ThermoplasticMaterials", *Polymer Preprints*, 731–733, Aug. 1993.
P.A. Rodgers and I.C. Sanchez, "Gas Solubility in Polymers and Blends", *Polymer Preprints*, 392–392. Aug. 1991.
I.C. Khoo, "Liquid Crystals Physical Properties and Non–linear Optical Phenomena", p. 5–11, 1995.
B. N. Epstein et al. "Polymer Blends—An Overview", *Polymer Preprints*, 42–43, Jun. 1991.
T. W. Cheng et al., "Property and Morphology Relationships for Ternary Blends of Polycarbonate, Brittle Polymers, and an Impact Modifier", *Polymer Preprints*, 58–59, Jun. 1991.
S. Allen et al., "The Effect of Additives on Tensile Properties of PPD–T Fibers", *Polymer Preprints*, 54–55, Jun. 1991.
M. Adur and L.J. Bonis, "PET–LCP Compatabilized Alloys: A New Unique Development".

(List continued on next page.)

Primary Examiner—Harold Pyon
Assistant Examiner—Chris Bruenjes
(74) Attorney, Agent, or Firm—Vidas, Arrett & Steinkraus

(57) ABSTRACT

A portion of a medical device formed from a melt blend of a polyesterimide anhydride liquid crystal polymer and at least one other polymer.

19 Claims, 1 Drawing Sheet

U.S. PATENT DOCUMENTS

| | | | |
|---|---|---|---|
| 4,130,545 A | 12/1978 | Calundann | 260/40 |
| 4,154,244 A | 5/1979 | Becker et al. | 128/349 |
| 4,161,470 A | 7/1979 | Calundann | 260/40 |
| 4,318,842 A | 3/1982 | East et al. | 524/605 |
| 4,331,786 A | 5/1982 | Foy et al. | 525/408 |
| 4,386,174 A | 5/1983 | Cogswell et al. | 524/27 |
| 4,433,083 A | 2/1984 | Cogswell et al. | 524/27 |
| 4,438,236 A | 3/1984 | Cogswell et al. | 525/165 |
| 4,444,817 A | 4/1984 | Subramanian | 428/36 |
| 4,468,364 A | 8/1984 | Ide | 264/176 |
| 4,490,421 A | 12/1984 | Levy | 428/35 |
| 4,954,606 A * | 9/1990 | Dicke et al. | 528/170 |
| 4,963,313 A | 10/1990 | Noddin et al. | 264/573 |
| 5,156,785 A | 10/1992 | Zdrahala | 264/108 |
| 5,195,969 A | 3/1993 | Wang et al. | 604/96 |
| 5,248,305 A | 9/1993 | Zdrahala | 604/280 |
| 5,254,089 A | 10/1993 | Wang | 604/96 |
| 5,264,260 A | 11/1993 | Saab | 428/35.5 |
| 5,270,086 A | 12/1993 | Hamlin | 428/35.2 |
| 5,290,306 A | 3/1994 | Trotta et al. | 606/194 |
| 5,304,340 A | 4/1994 | Downey | 264/521 |
| 5,306,246 A | 4/1994 | Sahatjian et al. | 604/96 |
| 5,328,468 A | 7/1994 | Kaneko et al. | 604/96 |
| 5,330,428 A | 7/1994 | Wang et al. | 604/96 |
| 5,348,538 A | 9/1994 | Wang et al. | 604/96 |
| 5,358,486 A | 10/1994 | Saab | 604/96 |
| 5,389,314 A | 2/1995 | Wang | 264/25 |
| 5,441,489 A | 8/1995 | Utsumi et al. | 604/280 |
| 5,447,497 A | 9/1995 | Sogard et al. | 604/101 |
| 5,456,674 A | 10/1995 | Bos et al. | 604/280 |
| 5,512,051 A | 4/1996 | Wang et al. | 604/96 |
| 5,554,120 A | 9/1996 | Chen et al. | 604/96 |
| 5,556,383 A | 9/1996 | Wang et al. | 604/96 |
| 5,565,530 A | 10/1996 | Hattori et al. | 525/419 |
| 5,587,125 A | 12/1996 | Roychowdhury | 264/515 |
| 5,647,848 A | 7/1997 | JØrgensen | 604/96 |
| 5,667,499 A | 9/1997 | Welch et al. | 604/282 |
| 5,677,394 A * | 10/1997 | Bohme et al. | 525/425 |
| 5,680,873 A | 10/1997 | Berg et al. | 128/772 |
| 5,704,913 A | 1/1998 | Abele et al. | 604/101 |
| 5,733,980 A | 3/1998 | Cozewith et al. | 525/314 |
| 5,759,647 A * | 6/1998 | Kuroda et al. | 428/34.5 |
| 5,807,327 A | 9/1998 | Green et al. | 604/96 |
| 5,830,182 A | 11/1998 | Wang et al. | 604/96 |
| 5,833,657 A | 11/1998 | Reinhardt et al. | 604/96 |
| 5,843,541 A * | 12/1998 | Alanko et al. | 428/35.7 |
| 5,976,120 A | 11/1999 | Chow et al. | 604/525 |
| 6,024,722 A | 2/2000 | Rau et al. | 604/96 |
| 6,045,547 A | 4/2000 | Ren et al. | 604/525 |
| 6,242,063 B1 | 6/2001 | Ferrera et al. | 428/35.2 |
| 6,284,333 B1 | 9/2001 | Wang et al. | 428/32.5 |
| 6,325,780 B1 | 12/2001 | Schaible et al. | 604/103.06 |
| 6,328,925 B1 | 12/2001 | Wang et al. | 264/512 |

OTHER PUBLICATIONS

G. C. Rutledge, "Modelling Chain Rigidity and Orientation in Liquid Crystalline Polymers", *Polymer Preprints*, 537–538 Apr. 1992.

M. M. Coleman et al., "Miscibility Maps for Copolymer—Copolymer Blends: A Comparison of Theoretical Predictions to Experimental Data", *Polymer Preprints*, 44–45, Jun. 1991.

M. M. Nir and R. E. Cohen, "Compatibilization of Blends of Crysatllizable Polybutadiene Isomers by Precipitation and by Addition of Amorphous Diblock Copolymer", *Polymer Preprints*, 60–61, Jun. 1991.

P. J. Collings, "Liquid Crystals, Nature's Delicate Phase of Matter", pp. 20–23, 162–180 (1990).

Kirk–Othmer Concise Encyclopedia of Chemical Technology, pp. 148–149, 391–395, 814–819, 924–939 (1985).

R. J. Lewis, Sr., Hawley's Condensed Chemical Dictionary, $12^{th}$ ed. pp. 704, 932–934, 936–939, (1993).

W. Brostow, "Properties of Polymer Liquid Crystals: Choosing Molecular Structures and Blending", *Polymer, vol. 31, 979–995*, Jun. 1990.

E. Barmatov et al., "Oriented Networks of Comb–Shaped Liquid Crystalline Polymers", *Polymer Preprints*, 706–707, Aug. 1993.

M. Brehmer et al., "LC–Elastomers by Chemical and Physical Crosslinking", *Polymer Preprints*, 708–709, Aug. 1993.

E. Okoroafor and J. Rault, "Cryodilation of Thermoplastic PEBA Elastomers", *J. Polymer Sci: Part B: Polymer Physics*, Vopl. 29, 1427–1436, 1991.

O.V. Noah and N. A. Plate, "Simulation of Macromolecules Confomations in Processes of Intra– and Intermolecular Crosslinking", *Polymer Preprints*, 578–579 Apr. 1992.

H. Boublil et al., "*Morphology of Polyamide and Polyether Block Amide Blends*", Polymer Engineering and Science, vol. 29, No. 10, 679–684, May 1989.

J.G. Harris and Y. Wang, "Molecular Dynamics Studies of Branched and Linear Hydrocarbons at Liquid–Vapor and Liquid–Solid Interfaces", *Polymer Preprints*, 539–540, Apr. 1992.

J. P deSouza et al., "Processing Studies of In Situ Composites base on Blends of Liquid Crystalline Polymers With Engineering Thermoplastics", *Polymer Preprints*, 392–393 Apr. 1992.

Q. Lin and A. F. Yee, Measurement of Molecular Orientation of Liquid Crystalline Polymer in situ Composites by X–Ray Scattering Technique, *Polymer Preprints*, pp. 298–99, Apr. 1992.

J. Liu et al., "Crystal Structure and Transistions in Rigid Rod Thermotropic Liquid Crystal Polymers", *Polymer Preprints*, 337–338 Apr. 1992.

W. J. Farrissey and T. M. Shah, Polyamide Thermoplastic Elastomers, in Handbook of Thermoplastic Elastomers. B. M. Walker and C.R. Rader, eds., pp. 258–281.

R. K. Menon, "Kinetic Theory for Liquid Crystalline Polymer Solutions", *Polymer Preprints*, 574–575 Apr. 1992

A. Y. Bilibin and A. R. Stepanova, "Synthesis of Liquid Crystalline Multiblock Copolymers With Definite Structure of Rigid Block", *Polymer Preprints*, 714–715, Aug. 1993.

R.R. Matheson, Jr., "Polymers, Processes and Additives as Systems", *Polymer Preprints*, 52–53, Jun. 1991.

J. R. Runt et al., "Phase Behavior and Crystallization in Blends of Poly(butleneterephthalate) and Polyarylate", *Polymer Preprints* 56–57, Jun. 1991.

U. M. Vakil and G. C. Martin, Analysis of Structure–Property Relations in Crosslinked Epoxies:, *Polymer Preprints*, 62–63, Jun. 1991.

Heinemann, K. "Novel Reactive LCPs As a Blend Component in Polyamide Fibers" Thuringisches Institut fur Textil.

Hoechst Celanese Vectra® Liquid Crystal Polymer Product Information.

P. Peyser, "Glass Transition Temperatures of Polymers" In Polymer Handbook $3^{rd}$ ed. J. Brandrup and E.H. Immergut eds., VI–258–259.

Superex Polymer, Inc Advertisment, "Building Product Valve through New Processing and Application Technologies".

D. H. Weinkauf and D. R. Paul, "The Influence of Molecular Architecture on Gas Transport Properties of Liquid Crystalline Polymers", Polymer Preprints, 372–373, Aug. 1991.

Amoco Engineering Plastic for Performance and Value Product Brochure.

W.M. Cheng et al., "Main Chain–Side Cahin Liquid Crystal Polymer Blends for Improved Physical Properties", *Polymer Preprints*, 50–51, Jun. 1991.

B. Miller, "Rotating Dies Paves Way for Extruding LCO", Plastics World.

Database WPI, Section Ch, Week 199030; Derwent Publications Ltd., London, GB; Class A26, AN 1990–2294428 XP002245776 & JP 02 159247 A (Sumitomo Bakelite Co) Jun. 19, 1990, Abstract.

* cited by examiner

BALLOONS MADE FROM LIQUID CRYSTAL POLYMER BLENDS

FIELD OF THE INVENTION

The present invention relates to novel liquid crystal polymer blends for use in medical devices.

BACKGROUND OF THE INVENTION

Catheter devices having a dilatation balloon mounted at the distal end of the catheter are useful in a variety of medical procedures. A balloon reservoir may be used to deliver a biologically compatible fluid, such as radiologically opaque fluid for contrast x-rays, to a site within the body. Radial expansion of a balloon may be used to expand or inflate a stent positioned within the body. A balloon may also be used to widen a vessel into which the catheter is inserted by dilating the blocked vessel. For example, in the technique of balloon angioplasty, a catheter is inserted for long distances into blood vessels of extremely reduced diameter and used to release or dilate stenoses therein by balloon inflation. These applications require thin walled high strength relatively inelastic balloons of accurately predictable inflation properties.

Depending on the intended use of the balloon and the size of the vessel into which the catheter is inserted, the requirements for strength and the size of the balloon vary widely. Balloon angioplasty has perhaps the most demanding requirements for such balloons. Typically, this application requires that the balloons have uniformly thin walls and a small diameter in their unexpanded state. The walls and waist thicknesses of the balloon limit the minimum diameter of the catheter distal end, and therefore determine the limits on minimum blood vessel diameter treatable by this method, as well as the ease of passage of the catheter through the vascular system.

Further requirements include high balloon strength which enables the balloon to push open a stenosis and to avoid bursting of the balloon under the high internal pressures necessary to inflate the balloon at the site of the stenosis. The balloon must also be sufficiently elastic to allow a surgeon to vary the diameter of the balloon as required to treat individual lesions. However, the balloon must have relatively low elasticity in order to accurately control the balloon diameter, and variations in pressure must not cause wide variations in balloon diameter.

These physical requirements may conflict with one another and thus can make the formation of a balloon from a single material difficult depending on the end use of the balloon. Various approaches have been taken including melt blending materials and the use of multilayer balloon structures.

Blends of liquid crystal polymers and thermoplastic non-LCP base polymers have been employed including polyesteramide and polyester-type LCPs, for example. See commonly assigned U.S. Pat. No. 6,242,063 and U.S. Pat. No. 6,284,333.

SUMMARY OF THE INVENTION

The present invention relates to the use of melt blending novel polyesterimide anhydride liquid crystal polymers (LCP-PA) with various other polymeric materials for use in catheter devices.

The polyesterimide anhydride liquid crystal polymers have terminal and/or lateral anhydride groups.

In some embodiments, the LCA-PA is melt blended with a polyester, a polyamide, a copolymer thereof or a mixture thereof. The mixture is suitable for use in making extruded tubular structures for use in portions of medical devices such as catheter shafts, dilatation balloons, and so forth.

DETAILED DESCRIPTIONS OF THE PREFERRED EMBODIMENTS

Figure 1:
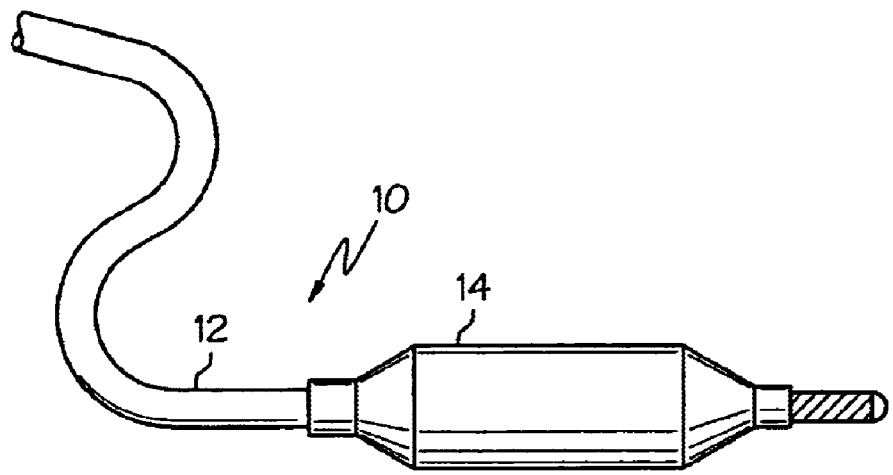
FIG. 1 is a side view of a catheter balloon according to the present invention.

The present invention relates to polymeric blends which include at least one liquid crystal polymer which is a polyesterimide anhydride (LCP-PA) and at least one other non-LCP base polymer. The polymeric blends are melt blended and include from about 0.1 wt-% to about 40 wt-% of the LCP-PA, suitably about 0.2 wt-% to about 20 wt-%, and most suitably about 0.5 wt-% to about 10 wt-% of the LCP-PA and from about 60 wt-% to about 99.9 wt-% of at least one second polymer, hereinafter referred to as a base polymer, which is not a liquid crystal polymer, suitably about 80 wt-% to about 99.8 wt-% and most suitably about 90 wt-% to about 99.5 wt-% of at least one base polymer.

The liquid crystal polymers (LCPs) useful herein may be characterized as meltable, reactive LCPs capable of forming covalent links with another polymer when mixed at elevated temperatures such as in an extruder or high shear mixer. The LCPs may be chemically characterized as polyesterimides having terminal and/or lateral anhydride groups (PCP-PA).

Polyesterimides having terminal anhydride groups may be prepared by reacting p-acetoxybenzoic acid (pAOBA), hydroquinone diacetate (HDAC), 6-(4-carboxyphthalimido)-n-hexanoic acid (CPIHA) and an excess of trimellitic acid anhydride (TMAA) which produces a polyesterimide having an anhydride group at each end.

A polyesterimide having lateral anhydride groups located along the polymer chain, as well as terminal anhydride groups, may be prepared by using the condensation product of 6-(4-carboxyphthalimido)-n-hexanoic acid (CPIHA) and 3,6-diacetoxy phthalic acid-1,2-anhydride (DAPAA). The resulting precondensate may then be used as a substitute for the 6-(4-carboxyphthalimido)-n-hexanoic acid. Using the precondensate rather than CPIHA results in a polyesterimide having both terminal and lateral anhydride groups.

The number of resultant anhydride groups as well as the molecular weight of the final LCP-PA may be varied by altering the ratio of CPIHA monomer to DAPAA monomer. The number of anhydride groups may be varied between about 4 and about 18 and molecular weight of about 30 kg/mol to about 80 kg/mol could be obtained. Suitably, the LCP-PA melts at a temperature of less than 275° C., suitably less than 250° C., and most suitably in the range of about 150° C. to 250° C.

The LCP-PA may then be blended with various other polymeric materials to impart higher strength and resistance to shrinkage to base polymer materials which have greater flexibility, softness or elasticity. Examples of polymeric materials with which the LCP-PA may be blended include, but are not limited to, polyamides, polyesters, nylons, and any copolymers thereof, as well as mixtures thereof. Suitably, the polymeric materials have melting temperatures between about 140° C. and about 275° C.

As used herein, the term "copolymer" shall be used to describe any polymeric material which is formed of two or more monomers.

Some specific examples of commercially available polyester copolymers useful in balloon formation include, for instance, poly(ester-block-ether) polymers such as HYTREL® available from DuPont de Nemours & Co.; ARNITEL® available from DSM; poly(ester-block-ester) polymers such as RITEFLEX® available from Hoechst-Celanese; and poly(ester-block-amide) polymers such as PEBAX® available from Atofina Engineering Polymers Division, North America.

Polyesters useful herein include the phthalate and naphthalate polyesters and copolyesters including, but not limited to polyalkylene terephthalates such as polyethylene terephthalate and polybutylene terephthalate; polyalkylene terephthalate/isophthalate copolyesters; polyalkylene naphthalate such as polyethylene naphthalate and polybutylene naphthalate; polyalkylene terephthalate/naphthalate copolyesters; and so forth. Examples of commercially available polyesters and copolyesters include polyethylene terephthalate homopolymers and copolymers such as copolyester Type T74 available from Hoechst Celanese; KODAR® A150 available from Eastman Kodak; polyesters available under the tradename of CLEARTUFF® such as CLEARTUFF® 8006 or TRAYTUFF® available from Shell Chemical Co.; and SELAR® PT available from DuPont de Nemours & Co.; PEN homopolymers and PEN/PET copolymers including, for example VITUF® SLX available from Shell Chemical, PEN homopolymer 14991 available from Eastman Chemical Co. and various PEN homopolymers and copolymers available from Teijin Ltd. in Tokyo, Japan under the designations TN8070, TN8060, TN8756T and TN8880N.

Examples of useful polyamides include, but are not limited to, nylons 11 and 12.

Particular balloon materials which are may be blended with the LCP-PA in accordance with the present invention include poly(ether-block-amides), such as PEBAX® 7033 or 7233; poly(ester-block-ethers) such as ARNITEL® EM 40; polyethylene terephthalate; and nylon. The formation of catheter balloons made of block copolymer elastomers where the hard segments are polyester or polyamide and the soft segments are polyether; is discussed in U.S. Pat. No. 5,556,383 issued Sep. 17, 1996 to Wang et al. incorporated by reference herein.

The polyesterimide anhydride LCP polymers are capable of forming graft polymers when melt blended at elevated temperatures with polyesters and polyamides. The LCP-PAs may react with certain types of base polymers such as polyesters, polyamides, and so forth, under the right conditions, to form graft polymers. For instance, at elevated temperatures which are standard for extrusion, graft polymers may form. Extrusion temperatures are commonly in the range of 200° C.–250° C. or higher, although lower or higher temperatures may be employed as well. Furthermore, graft polymers may form at any elevated temperature but the extent of formation of the graft may vary.

Additionally, the composition may include other optional ingredients known to those of skill in the art including other polymeric materials.

The resultant melt blended compositions may be employed in medical devices such as catheter assemblies. In particular, the compositions may be employed for balloon formation or catheter shafts.

The melt blended composition is particularly suitable for use in dilatation balloons used for percutaneous transluminal angioplasty and other minimally invasive procedures. The balloon diameter for such applications is typically from about 1.5 to about 30 mm, depending on the exact use. The wall thickness of the balloon is typically between about 0.0002" and 0.0020".

The balloons of the invention may be either single layer balloons or they may be multilayer balloons.

In one embodiment, the balloon material is substantially non-compliant, providing a radial expansion of less than about 5%, suitably less than about 4% when inflation pressure is increased from about 4 atm to about 10 atm.

Balloon formation may be carried out in any conventional manner with conventional extrusion and blowing techniques, but basically there are three major steps in the process which include extruding a tubular preform or parison, blow molding the balloon and annealing the balloon. Depending on the balloon material employed, the preform may be axially stretched before it is blown. The balloons may also be optionally oriented by what is referred to in the industry as machine orientation during extrusion as known in the art. Techniques for balloon formation are discussed in U.S. Pat. No. 4,490,421 to Levy and in U.S. Pat. No. 5,348,538 issued Sep. 20, 1994 to Wang et al.

FIG. 1 illustrates generally at 10, a catheter having a balloon 14 formed of the melt blend product of the present invention and an elongated tube 12 which also may optionally be formed of the melt blend product of the present invention.

Figure 2:
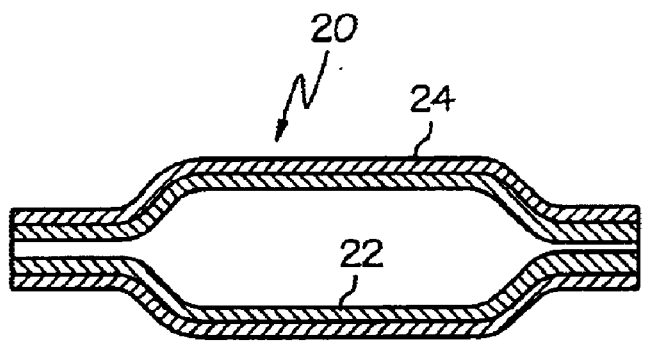
FIG. 2 is a side view of a dual layer dilatation balloon according to the present invention.

FIG. 2 illustrates an alternative embodiment of the present invention in which catheter balloon 20 is formed of a dual layer structure in which the inner layer 22 is formed of the melt blend product of the present invention and the outer layer 24 is formed of a different polymer material, for instance, a relatively soft elastomeric polymer such as poly(ester-block-ether), poly(ester-block-ester) or poly(ester-block-amide).

Figure 3:
FIG. 3 is a side view of a tubular structure according to the present invention.

The present invention may be of course used for the extrusion of any tubular structures useful in medical devices. FIG. 3 illustrates a tubular structure 15 formed of the melt blend product of the present invention which may be used as a catheter shaft, among others.

The above disclosure is not exhaustive and is intended for illustrative purposes only and thus is not intended to limit the scope of the present invention. This description will suggest many variations and alternatives to one of ordinary skill in this art. Those familiar with the art may recognize other equivalents to the specific embodiments described herein which equivalents are also intended to be encompassed by the claims.

What is claimed is:

1. A medical device at least a portion of which is composed of a polymeric material which is a melt blend product comprising:
   a) at least one polyesterimide anhydride liquid crystal polymer; and
   b) at least one base polymer.

2. The medical device of claim 1 wherein said polyesterimide anhydride liquid crystal polymer has terminal and lateral anhydride groups.

3. The medical device of claim 1 wherein said polyesterimide anhydride liquid crystal polymer has about 4 to about 18 anhydride groups per molecule.

4. The medical device of claim 1 wherein said at least one base polymer is a polyamide, a polyester, a copolymer thereof, or mixture thereof.

5. The medical device of claim 1 wherein said at least one base polymer is a poly(ether-block-amide), a poly(ester-block-ether), a polyethyleneterephthalate, nylon 11, nylon 12, or mixture thereof.

6. The medical device of claim 1 wherein said polyesterimide anhydride liquid crystal polymer and said at least one base polymer react to form a graft polymer.

7. The medical device of claim 1 wherein said medical device is a catheter.

8. The medical device of claim 1 wherein said portion of said medical device is a balloon mounted on a catheter.

9. The medical device of claim 1 wherein said portion of said medical device is a catheter shaft.

10. The medical device of claim 1 wherein said melt blend product comprises about 0.1 wt-% to about 40 wt-% of said liquid crystal polymer and about 60 wt-% to about 99.9 wt-% of at least one other polymer.

11. The medical device of claim 1 wherein said melt blend product comprises about 0.5 wt-% to about 10 wt-% of said liquid crystal polymer and about 90 wt-% to about 99.5 wt-% of at least one other polymer.

12. A dilatation balloon formed from an extruded tubular parison which is a melt blend product of at least one polyesterimide anhydride liquid crystal polymer and at least one other polymer.

13. The dilatation balloon of claim 12 wherein said polyesterimide has terminal and lateral anhydride groups.

14. The dilatation balloon of claim 12 wherein said at least one other polymer is a polyester, a polyamide, a copolymer thereof or a mixture thereof.

15. The dilatation balloon of claim 12 wherein said at least one other polymer is a poly(ester-block-ether), a poly(ether-block-amide), polyethyleneterephthalate, nylon 11, nylon 12, or mixture thereof.

16. The dilatation balloon of claim 12 wherein said polyesterimide anhydride liquid crystal polymer and at least one other polymer form a graft polymer.

17. The dilatation balloon of claim 12 wherein said melt blend product comprises about 0.1 wt-% to about 40 wt-% of said polyesterimide anhydride liquid crystal polymer and about 60 wt-% to about 99.9 wt-% of at least one other polymer.

18. The dilatation balloon of claim 12 wherein said melt blend product comprises about 0.5 wt-% to about 10 wt-% of said polyesterimide anhydride liquid crystal polymer and about 90 wt-% to about 99.5 wt-% of at least one other polymer.

19. The dilatation balloon of claim 12 wherein said polyesterimide anhydride has about 4 to about 18 anhydride groups per molecule.

* * * * *